(12) United States Patent
Jiang et al.

(10) Patent No.: US 10,039,824 B2
(45) Date of Patent: Aug. 7, 2018

(54) TRADITIONAL CHINESE MEDICINE MULBERRY LEAVES POLYSACCHARIDE AND EUCOMMIA POLYSACCHARIDE IMMUNOSTIMULANT AND APPLICATION THEREOF

(71) Applicant: Jiangsu Agri-animal Husbandry Vocational College, Taizhou (CN)

(72) Inventors: Chunmao Jiang, Taizhou (CN); Xiaolan Chen, Taizhou (CN); Deyun Wang, Taizhou (CN); Haifeng Yang, Taizhou (CN); Caihong Wu, Taizhou (CN); Yi Zheng, Taizhou (CN); Jianhua Dai, Taizhou (CN); Wei Chen, Taizhou (CN); Xianglai He, Taizhou (CN)

( * ) Notice: Subject to any disclaimer, the term of this patent is extended or adjusted under 35 U.S.C. 154(b) by 102 days.

(21) Appl. No.: 15/206,226

(22) Filed: Jul. 9, 2016

(65) Prior Publication Data
US 2016/0317655 A1    Nov. 3, 2016

Related U.S. Application Data

(63) Continuation-in-part of application No. PCT/CN2014/001033, filed on Nov. 19, 2014.

(30) Foreign Application Priority Data

Jan. 9, 2014    (CN) .......................... 2014 1 0010826

(51) Int. Cl.
| | | |
|---|---|---|
| *A61K 36/00* | (2006.01) |
| *A61K 39/39* | (2006.01) |
| *A61K 36/46* | (2006.01) |
| *A61K 36/605* | (2006.01) |
| *C08B 37/00* | (2006.01) |
| *C12N 7/00* | (2006.01) |
| *A61K 39/12* | (2006.01) |
| *A61K 39/00* | (2006.01) |
| *A61K 39/17* | (2006.01) |

(52) U.S. Cl.
CPC ............. *A61K 39/39* (2013.01); *A61K 36/46* (2013.01); *A61K 36/605* (2013.01); *C08B 37/0003* (2013.01); *C12N 7/00* (2013.01); *A61K 39/12* (2013.01); *A61K 39/17* (2013.01); *A61K 2039/552* (2013.01); *A61K 2039/55583* (2013.01); *A61K 2039/55588* (2013.01); *A61K 2039/575* (2013.01); *C12N 2760/18134* (2013.01); *C12N 2770/10034* (2013.01)

(58) Field of Classification Search
CPC ..................................................... A61K 36/00
See application file for complete search history.

(56) References Cited

FOREIGN PATENT DOCUMENTS

CN    101524114 A   *   9/2009

* cited by examiner

*Primary Examiner* — Qiuwen Mi
(74) *Attorney, Agent, or Firm* — Wayne & Ken, LLC; Tony Hom

(57) ABSTRACT

A traditional Chinese medicine immunopotentiator prepared from mulberry leaves polysaccharide and eucommia polysaccharide. The immunopotentiator can stimulate proliferation of chicken lymphocytes in vitro. When used together with newcastle disease vaccine to immunize chickens, the immunopotentiator can increase serum antibody titer, promote proliferation of lymphocytes, and enhance cellular immunity and humoral immunity of the chickens. When used together with porcine productive and respiratory syndrome vaccine to immunize piglets, the immunopotentiator can increase the serum antibody titer. When used together with the porcine productive and respiratory syndrome vaccine to immunize layers, the immunopotentiator can increase porcine productive and respiratory syndrome virus yolk antibody titer and improve immune effects of the vaccine.

5 Claims, No Drawings

TRADITIONAL CHINESE MEDICINE MULBERRY LEAVES POLYSACCHARIDE AND EUCOMMIA POLYSACCHARIDE IMMUNOSTIMULANT AND APPLICATION THEREOF

CROSS-REFERENCE TO RELATED APPLICATIONS

This application is a continuation in part of International Patent Application No. PCT/CN2014/001033 with a filing date of Nov. 19, 2014, designating the United States, now pending, and further claims priority to Chinese Patent Application No. 201410010826.6 with a filing date of Jan. 9, 2014. The content of the aforementioned applications, including any intervening amendments thereto, are incorporated herein by reference.

TECHNICAL FIELD

The invention relates to a traditional Chinese medicine immunopotentiator, prepared from mulberry leaves polysaccharide and eucommia polysaccharide, which belongs to technical field of immune adjuvant of livestock and poultry,

BACKGROUND OF THE PRESENT INVENTION

Animals' viral infectious diseases such as highly pathogenic avian influenza, newcastle disease and infectious bursal disease, harm the development of livestock husbandry seriously, cause great economic loss and has received extensive attention of the world. Immunization is the best measure to prevent and control the outbreak of these diseases. However, inoculation of vaccine solely usually produces relative weak immunity. Immune adjuvant can enhance immune effects of the vaccine, and prolong protection time. Many immune adjuvants, such as freund's adjuvant and lipopolysaccharide, are easy to cause systematic responses (such as nausea, fever, anaphylaxis, eosinophilia, toxicosis, paralysis and autoimmune disease) and local inflammatory responses (such as inflammation, pain, swelling, necrosis, ulceration and abscessus), so the extensive application is limited, Therefore, the development of efficient and safe new immune adjuvant has become the hotspot of preventing and controlling animal-borne disease. It is proved many traditional Chinese medicines have immunological enhancement, efficient and safe. However, most of them have complicated components and inconvenient administration. With the development of intensive livestock farming, drinking and administration of animal population has more obvious advantages. The invention carries out component medicine screening, prescription screening, and dose screening, combined some aspects such as convenient for application, to perform comprehensive comparison, and the immunopotentiator prepared from mulberry leaves polysaccharide and eucommia polysaccharide is developed ultimately.

SUMMARY OF PRESENT INVENTION

The invention aims to the problem of urgent need of efficient and safe immunopotentiator or vaccine adjuvant in current animal epidemic disease prevention and control technology, and provides a new traditional Chinese medicine immunopotentiator prepared from mulberry leaves polysaccharide and eucommia polysaccharide.

A new traditional Chinese medicine immunopotentiator of the invention is characterized in that each 1000 ml of medicinal liquid is prepared from 150 g of mulberry leaves and 145 g of eucommia bark. The content of the mulberry leaves polysaccharide in medicinal liquid is not lower than 0.2%, and the content of the eucommia polysaccharide is not lower than 0.1%.

The processes of producing each 1000 ml of medicinal liquid are as follows: decocting mulberry leaves with water for 2 times, ethanol precipitation, drying ethanol sediments, dissolving with 640 mL of water, and obtaining mulberry leaves polysaccharide solution; degreasing eucommia, ethanol precipitation, drying ethanol sediments, dissolving with water, and obtaining eucommia polysaccharide solution, mixing two solutions evenly, subpackaging and obtaining the medicinal liquid.

The extraction process of the mulberry leaves polysaccharide is adding 30 time of water to decoct the mulberry leaves for 2 times, 1.5 hour for the first time and 1 hour for the second time. The extraction process of the eucommia polysaccharide is adding 4 time of absolute ethyl alcohol to perform reflux degreasing to the eucommia bark for 2 times and decocting with water for 2 times, 1.5 hour for the first time and 1 hour for the second time.

Beneficial effects: the invention is choosing traditional Chinese medicine polysaccharides with immunological enhancement, comparing and selecting mulberry leaves polysaccharide and eucommia polysaccharide which have better effect, forming multiple compounds by different ratio, proving the effect of compounds is better than that of single medicine by serial tests, and selecting the ratio with best effect (Table 1).

The ordinary skill in the art can determine the extraction condition of the mulberry leaves polysaccharide and eucommia polysaccharide by orthogonal test, and can determine the production process of immunopotentiator prepared from mulberry leaves polysaccharide and eucommia polysaccharide by optimizing solubility condition of polysaccharides.

Compared with the prior art, the advantages of the invention are as follows:

1. Compared with chemical adjuvants, the immunopotentiator prepared from mulberry leaves polysaccharide and eucommia polysaccharide has reliable effect, derived from natural traditional Chinese medicine, it has no toxicity, no side effects, and no medicinal residue, which ensures safety of animal-derived food, and its production has no pollution to the environment and complies with the green and environmental protection requirement.

2. Compared with traditional Chinese medicine prescription, the immunopotentiator prepared from mulberry leaves polysaccharide and eucommia polysaccharide has refine prescription, definite components. simplified process, controllable quality, convenient administration and low cost.

3. Compared with the same kind compositions of traditional Chinese medicine prescription, the efficiency of the immunopotentiator prepared from mulberry leaves polysaccharide and eucommia polysaccharide is improved, when used together with newcastle disease vaccine to immunize chickens, the immunopotentiator can enhance cellular immunity and humoral immunity, and improve immune effects of the vaccine.

DETAILED DESCRIPTION OF PREFERRED EMBODIMENTS

1. Preparation Process (1) the preparation of mulberry leaves polysaccharide is taking mulberry leaves polysaccharide yield in extract as index, carrying out orthogonal test to water addition, extraction time, extraction times, and ethanol concentration for ethanol precipitation, and determining the best extraction process of the mulberry leaves polysaccharide is adding 30 times of water, decocting for 2 times, 1.5 h for the first time and 1h for the second time. Taking 150 g of mulberry leaves, water decocting by above process, merging of filtrates, adding 95% of ethanol so that ethanol content can reach 75%, still standing for 12 h, precipitating, drying under 65 DEG C, dissolving with 640 mL of water and obtaining mulberry leaves polysaccharide water solution.

(2) the preparation of eucommia polysaccharide is taking eucommia polysaccharide yield in extract as index, carrying out orthogonal test to degreasing ethanol content, water addition, extraction time, and extraction times, and determining the best extraction process of the eucommia polysaccharide is adding 4 time of 95% of ethanol to perform reflux degreasing for 2 times, adding 20 time of water to decoct for 2 times, 1.5 h for the first time and 1 h for the second time, Taking 145 g of eucommia bark and degreasing by above process, water decocting, merging of filtrates, adding 95% of ethanol so that ethanol content can reach 75%, still standing for 12 h, precipitating, drying under 65 DEG C, dissolving with 360 mL of water and obtaining mulberry leaves polysaccharide water solution.

(3) the preparation of the medicinal liquid is mixing the mulberry leaves polysaccharide solution and eucommia polysaccharide solution, and subpackaging. The polysaccharide content is determined by phenol-sulfuric acid method, and the content of rutin and pinoresinol diglucoside is determined by HPLC method. The polysaccharides content in the medicinal liquid is not lower than 0.3%, rutin content is not lower than 0.025% and the content of pinoresinol diglucoside is not lower than 0.01%.

2. Comparison of Enhancing Immune Effect (1) Enhancing Immune Effect in Virtu

Taking the immunopotentiator prepared from mulberry leaves polysaccharide and eucommia polysaccharide as test materials, preparing contrast prescription 1 (mulberry leaves extract and eucommia polysaccharide) and contrast prescription 2 (mulberry leaves polysaccharide and 2 parts of eucommia extract), first determining the safe concentration of three prescriptions to peripheral blood lymphocyte of chickens, diluting three prescriptions with cell culture medium (RPMI 1640) into 5 working concentrations, that is, 250 µg/mL$^{-1}$, 125 µg/mL$^{-1}$, 62.5 µg/mL$^{-1}$, 31.25 µg/mL$^{-1}$ and 15,625 µg/mL$^{-1}$ respectively, adding into cultured peripheral blood lymphocyte of chickens respectively, determining lymphocyte proliferation ($A_{570}$ value) by MTT method, taking $A_{570}$ value as index of lymphocyte proliferation, and calculating Stimulation Index (SI) of lymphocyte to compare the effect of three prescriptions based on formula: SI (medicine group $A_{570}$ value minus cell control group $A_{570}$ value)/cell control group $A_{570}$ value (wherein A is an average value).

Result: 1) change of lymphocyte proliferation: when the concentration of the immunopotentiator prepared from mulberry leaves polysaccharide and eucommia polysaccharide is 250 µg/mL$^{-1}$, 125 µg/mL$^{-1}$, 62.5 µg/mL$^{-1}$, and 31.25 µg/mL$^{-1}$, $A_{570}$ values of the immunopotentiator are much higher than that of the cell control group (P<0.05), and when the concentration of the contrast prescription 1 and the contrast prescription 2 is 50 µg/mL$^{-1}$, 125 µg/mL$^{-1}$, and 62.5 µ/mL$^{-1}$, $A_{570}$ values of the contrast prescription 1 and the contrast prescription 2 are much higher than that of the cell control group (P<0.05).

TABLE 1

CHANGE OF LYMPHOCYTE PROLIFERATION OF EACH GROUP ($A_{570}$ VALUE)

| Concentration (µg · mL$^{-1}$) | Immunopotentiator | Contrast prescription 1 | Contrast prescription 2 |
|---|---|---|---|
| 250 | 0.324 ± 0.003$^{ab}$ | 0.280 ± 0.003$^{b}$ | 0.290 ± 0.004$^{b}$ |
| 125 | 0.329 ± 0.001$^{a}$ | 0.295 ± 0.002$^{ab}$ | 0.298 ± 0.005$^{ab}$ |
| 62.5 | 0.312 ± 0.003$^{b}$ | 0.306 ± 0.003$^{a}$ | 0.307 ± 0.003$^{a}$ |
| 31.25 | 0.280 ± 0.001$^{c}$ | 0.263 ± 0.006$^{c}$ | 0.265 ± 0.004$^{c}$ |
| 15.625 | 0.252 ± 0.002$^{de}$ | 0.249 ± 0.003$^{cd}$ | 0.251 ± 0.007$^{cd}$ |
| Cell control group | 0.245 ± 0.003$^{e}$ | 0.245 ± 0.003$^{cd}$ | 0.245 ± 0.003$^{cd}$ |

Note:
marks without containing the same letter within the same line have significant difference(P < 0.05), so do the following tables.

2) Comparison of lymphocyte simulation index: when the concentration of the immunopotentiator prepared from mulberry leaves polysaccharide and eucommia polysaccharide is 250 µg/mL$^{-1}$, 125 µg/mL$^{-1}$, 62.5 µg/mL$^{-1}$, and 31.25 µg/mL$^{-1}$, the simulation index of the immunopotentiator is much higher than that of two contrast prescription groups (P<0.05), when the concentration of the immunopotentiator is 15.625 µg/mL$^{-1}$, the simulation index of the immunopotentiator is a little higher than that of two contrast prescription groups (Table 2).

TABLE 2

COMPARISON OF LYMPHOCYTE PROLIFERATION EFFECT SIMULATION OF EACH PRESCRIPTION (SI)

| | Concentration (µg · mL$^{-1}$) | | | | |
|---|---|---|---|---|---|
| Groups | 250 | 125 | 62.5 | 31.25 | 15.625 |
| Immunopotentiator | 1.321 ± 0.031$^{a}$ | 1.342 ± 0.011$^{a}$ | 1.273 ± 0.031$^{a}$ | 1.143 ± 0.011$^{a}$ | 1.029 ± 0.024$^{a}$ |
| Contrast prescription 1 | 1.142 ± 0.033$^{b}$ | 1.205 ± 0.022$^{b}$ | 1.251 ± 0.032$^{b}$ | 1.073 ± 0.04$^{b}$ | 1.018 ± 0.033$^{a}$ |
| Contrast prescription 2 | 1.183 ± 0.041$^{b}$ | 1.216 ± 0.051$^{b}$ | 1.253 ± 0.031$^{b}$ | 1.082 ± 0.041$^{b}$ | 1.024 ± 0.031$^{a}$ |

2) Enhancing Immune Test in Vivo

Method: taking the immuncpotentiator prepared from mulberry leaves polysaccharide and eucommia polysaccharide as test materials, preparing contrast prescription 1

(mulberry leaves extract and eucommia polysaccharide) and contrast prescription 2 (mulberry leaves polysaccharide and 2 parts of eucommia extract). Taking 150 14-day-old nonimmune and healthy Roman chickens, dividing into 5 groups randomly, dropwise adding 2 plumes of the newcastle disease IV vaccine into nose and eyes of each chicken except the Blank Control (BC) group to carry out first immunization, and carrying out second immunization on 28-day-old. At the same time of the first immunization and the second immunization, drinking water and administering corresponding drugs for 3 days for the chickens of three groups of traditional Chinese medicine, and drinking freely for the chickens of Vaccine Control (VC) and BC, and selecting six chickens of each group randomly on the 7$^{th}$ day ($D_7$), 14$^{th}$ day ($D_{14}$), 21th day ($D_{21}$) and 28$^{th}$ day ($D_{28}$) after immunization, collecting blood, separating serum, detecting ND-HI antibody titer by β-micromethod, and determining peripheral blood T lymphocyte proliferation by MTT method.

Result:

1) The antibody titer of the immunopotentiator prepared from mulberry leaves polysaccharide and eucommia polysaccharide at different time points after immunization is the highest, on $D_{14}$ after first immunization, the antibody tier is 0.53 titer higher than that of contrast prescription 2, and is much higher than that of other groups (P<0,05): on $D_{21}$ after first immunization, the antibody titer of the immunopotentiator is much higher than that of other groups, 1.43 titer higher than that of contrast prescription 1 and 1.09 titer higher than that of contrast prescription 2 respectively; on $D_{28}$ after first immunization, the antibody titer of the immunopotentiator is much higher than that of other groups, 1.43 titer higher than that of contrast prescription 1 and 1.23 titer higher than that of contrast prescription 2 respectively (Table 3), which shows the immunopotentiator prepared from mulberry leaves polysaccharide and eucommia polysaccharide can increase serum antibody titer greatly, and its effect is superior than other two contrast prescriptions.

TABLE 3

DYNAMIC CHANGE OF ANTIBODY TITER OF EACH GROUP

| Groups | $D_7$ | $D_{14}$ | $D_{21}$ | $D_{28}$ |
|---|---|---|---|---|
| Immunopotentiator | 4.78 ± 0.32 | 55.16 ± 0.23$^a$ | 7.21 ± 0.33$^a$ | 6.77 ± 0.28$^a$ |
| Contrast prescription 1 | 4.21 ± 0.21 | 4.29 ± 0.31$^b$ | 5.78 ± 0.42$^{bc}$ | 5.34 ± 0.32$^b$ |
| Contrast prescription 2 | 4.59 ± 0.31 | 4.63 ± 0.32$^{ab}$ | 6.12 ± 0.32$^{bc}$ | 5.54 ± 0.21$^b$ |
| VC | 3.82 ± 0.23 | 3.64 ± 0.31$^c$ | 5.09 ± 0.33$^c$ | 4.34 ± 0.27$^c$ |
| BC | 2.48 ± 0.21 | 2.29 ± 0.33$^d$ | 2.15 ± 0.21$^d$ | 2.14 ± 0.21$^d$ |

2) Change of Lymphocyte Proliferation

The $A_{570}$ value of the immunopotentiator prepared from mulberry leaves polysaccharide and eucommia polysaccharide at 4 time points after first immunization is the highest, on $D_7$ after first immunization, the $A_{570}$ value is much higher than that of VC and BC (PK0.05), and a little higher than that of two contrast prescriptions; on $D_{14}$ and $D_{28}$ after first immunization, the $A_{570}$ value is, much higher than that of contrast prescription 1 (P<0.05), and a little higher than that of contrast prescription 2; and on $D_{21}$ after first immunization, the $A_{570}$ value is much higher than that of other groups (P<0.05) (Table 4).

TABLE 4

DYNAMIC CHANGE OF LYMPHOCYTE PROLIFERATION OF EACH GROUP ($A_{570}$)

| Groups | $D_7$ | $D_{14}$ | $D_{21}$ | $D_{28}$ |
|---|---|---|---|---|
| Immunopotentiator | 0.257 ± 0.006$^a$ | 0.313 ± 0.012$^a$ | 0.319 ± 0.005$^a$ | 0.291 ± 0.013$^a$ |
| Contrast prescription 1 | 0.252 ± 0.012$^{ab}$ | 0.289 ± 0.008$^b$ | 0.298 ± 0.007$^b$ | 0.278 ± 0.005$^b$ |
| Contrast prescription 2 | 0.250 ± 0.007$^{ab}$ | 0.301 ± 0.013$^{ab}$ | 0.301 ± 0.012$^b$ | 0.285 ± 0.007$^{ab}$ |
| VC | 0.207 ± 0.005$^c$ | 0.238 ± 0.011$^c$ | 0.253 ± 0.003$^c$ | 0.241 ± 0.0074$^c$ |
| BC | 0.172 ± 0.021$^d$ | 0.1831 ± 0.009$^d$ | 0.179 ± 0.011$^d$ | 0.202 ± 0.004$^d$ |

Above results show when used together with newcastle'-disease vaccine to immunize chickens, the immunopotentiator can promote proliferation of lymphocytes, enhance cellular immunity of the chickens, and improve immune effects of the newcastle disease vaccine.

3. Selecting the best dose of the immunopotentiator prepared from mulberry leaves polysaccharide and eucommia polysaccharide Method: taking 210 14-day-old nonimmune and healthy Roman chickens, dividing into 9 groups randomly, dropwise adding 2 plumes of the newcastle disease IV vaccine into nose and eyes of each chicken except the Blank Control (BC) group to carry out first immunization, and carrying out second immunization on 28-day-old. At the same time of first immunization and second immunization, drinking water and administering corresponding drugs for 3 days based on 8 mg, 6 mg, 4 mg, 2 mg and 1 mg for each cock of 5 dose groups, and drinking freely for the chickens of Vaccine Control (VC) and BC, and selecting six cocks of each group randomly on $D_7$, $D_{14}$, $D_{21}$ and $D_{28}$ after immunization, collecting blood, separating serum, detecting ND-HI antibody titer by β-micromethod, and determining peripheral blood T lymphocyte proliferation by MTT method.

Result: 1) change of serum antibody titer: the antibody titer of each dose group of the immunopotentiator prepared from mulberry leaves polysaccharide and eucommia polysaccharide at different time points is much higher than that of VC and BC. On $D_7$ after first immunization, the antibody titer of 4 mg dose group is the highest, much higher than 2 mg and 1 mg dose group (P<0.05); on $D_{14}$ after first immunization, the antibody titer of 6 mg dose group is the highest, and the antibody titer of 4 mg does group, 6 mg does group and 8 mg does group are all much higher than that of other groups (P<0.05); on $D_{21}$ and $D_{28}$ after first immunization, the antibody titer of 4 mg does group, much higher than other groups (P <0.05) (Table 5).

TABLE 5

CHANGE OF SERUM ND-HI ANTIBODY TITER OF EACH GROUP (LOG$_2$)

| Groups | $D_7$ | $D_{14}$ | $D_{21}$ | $D_{28}$ |
|---|---|---|---|---|
| 8 mg | $4.92 \pm 0.33^a$ | $5.16 \pm 0.23^a$ | $6.52 \pm 0.31^b$ | $5.74 \pm 0.21^b$ |
| 6 mg | $4.79 \pm 0.32^{ab}$ | $5.31 \pm 0.32^a$ | $6.84 \pm 0.42^b$ | $6.12 \pm 0.32^b$ |
| 4 mg | $4..98 \pm 0.23^a$ | $5.28 \pm 0.26^a$ | $7.25 \pm 0.34^a$ | $6.76 \pm 0.34^a$ |
| 2 mg | $4.50 \pm 0.37^b$ | $4.86 \pm 0.26^b$ | $6.18 \pm 0.21^b$ | $5.49 \pm 0.32^{bc}$ |
| 1 mg | $4.33 \pm 0.21^b$ | $4.77 \pm 0.35^b$ | $5.33 \pm 0.22^c$ | $5.11 \pm 0.17^c$ |
| VC | $3.78 \pm 0.25^c$ | $4.34 \pm 0.33^c$ | $5.09 \pm 0.27^c$ | $4.77 \pm 0.24^d$ |
| BC | $2.39 \pm 0.23^d$ | $2.31 \pm 0.37^d$ | $2.13 \pm 0.21^d$ | $2.15 \pm 0.33^e$ |

2) Change of lymphocyte proliferation: the $A_{570}$ value of each dose group of the immunopotentiator prepared from mulberry leaves polysaccharide and eucommia polysaccharide at different time points is much higher than that of VC and BC. On $D_7$ after first immunization, $A_{570}$ values of three dose groups of the immunopotentiator are all much higher than that of VC (P<0.05): on $D_{14}$, $A_{570}$ values of 4 mg dose group and 6 mg dose group are much higher than that of VC and BC(P<0.05); on $D_{21}$, A570 values of 4 mg dose group and 6 mg dose group are much higher than that of other three groups (P<0.05): on $D_{28}$, $A_{570}$ value of 4 mg dose group are much higher than that of other groups (P<0.05) (Table 6).

TABLE 6

CHANGE OF LYMPHOCYTE PROLIFERATION

| Groups | $D_7$ | $D_{14}$ | $D_{21}$ | $D_{28}$ |
|---|---|---|---|---|
| 6 mg | $0.212 \pm 0.002^{ab}$ | $0.226 \pm 0.003^a$ | $0.224 \pm 0.007^a$ | $0.264 \pm 0.001^b$ |
| 4 mg | $0.217 \pm 0.003^a$ | $0.235 \pm 0.007^a$ | $0.241 \pm 0.003^a$ | $0.289 \pm 0.003^a$ |
| 2 mg | $0.203 \pm 0.004^b$ | $0.215 \pm 0.010^{ab}$ | $0.199 \pm 0.005^b$ | $0.265 \pm 0.002^b$ |
| VC | $0.187 \pm 0.003^c$ | $0.193 \pm 0.004^{bc}$ | $0.197 \pm 0.003^b$ | $0.250 \pm 0.003^b$ |
| BC | $0.192 \pm 0.004^c$ | $0.189 \pm 0.007^c$ | $0.167 \pm 0.001^c$ | $0.201 \pm 0.008^c$ |

Above results show the immunopotentiator prepared from mulberry leaves polysaccharide and eucommia polysaccharide can increase serum antibody titer of newcastle disease vaccine to immunize chickens, promote proliferation of peripheral blood lymphocyte, and enhance cellular immunity and humoral immunity of the chickens, and improve the immune effect of newcastle disease significantly; compared with other doses, 4 mg of drinking and administration of chickens is the best.

The above disclosure merely shows several specific embodiments of the invention, and the invention is not limited thereto. Any variations or substitution that may come into the mind of those skilled in the art without creative labor shall fail into the protection scope of the invention. Therefore, the protection scope of the invention shall be limited by the claims.

We claim:

1. A traditional Chinese medicine immunopotentiator, characterized in that it is prepared from mulberry leaves polysaccharide and eucommia polysaccharide, each 1000 ml of the immunopotentiator is prepared from 150 g of mulberry leaves and 140 g of eucommia bark;

the immunopotentiator comprises or comprises no additional Chinese traditional medicine extract;

the immunopotentiator contains no other chemical active ingredients;

processes of producing each 1000 ml of medicinal liquid are as follows:

decoding mulberry leaves with water for 2 times, ethanol precipitation, drying ethanol sediments, dissolving with 640 mL of water, and obtaining mulberry leaves polysaccharide solution;

degreasing eucommia, ethanol precipitation, drying ethanol sediments, dissolving with water, and obtaining eucommia polysaccharide solution, mixing the mulberry leaves polysaccharide solution and the eucommia polysaccharide solution evenly, subpackaging and obtaining the medicinal liquid;

extraction process of mulberry leaves polysaccharide is:

adding 30 times of water to decoct the mulberry leaves for 2 times, 1.5 hour for a first time and 1hour for a second time;

extraction process of eucommia polysaccharide are:

adding 4 times of absolute ethyl alcohol to perform reflux degreasing to the eucommia bark for 2 times and decocting with water for 2 times, 1.5 hours for a first time and 1 hour for a second time.

2. The traditional Chinese medicine immunopotentiator according to claim 1, characterized in that a content of mulberry leaves polysaccharide in medicinal liquid is between 0.2-0.6% and a weight percentage of the eucommia polysaccharide is between 0.1-0.5%.

3. A vaccine kit, characterized in that the vaccine kit comprises the traditional Chinese medicine immunopotentiator of claim 1.

4. The vaccine kit according to claim 3, wherein the vaccine kit comprises newcastle disease vaccine, the traditional Chinese medicine immunopotentiator is existed in the vaccine kit at a rate of each unit dose of the vaccine and 1 ml traditional Chinese medicine immunopotentiator.

5. An application of the traditional Chinese medicine immunopotentiator according to claim 1 in preparing medicines enhancing vaccine immunity; wherein the vaccine is newcastle disease vaccine.

* * * * *